United States Patent [19]
Croce et al.

[11] Patent Number: 5,695,944
[45] Date of Patent: Dec. 9, 1997

[54] MODULATION OF BCL-2 PHOSPHORYLATION

[75] Inventors: Carlo M. Croce, Philadelphia; Subrata Haldar, Springfield, both of Pa.

[73] Assignee: Thomas Jefferson University, Philadelphia, Pa.

[21] Appl. No.: 435,484

[22] Filed: May 5, 1995

[51] Int. Cl.$^6$ .................. G01N 33/567; G01N 33/574; G01N 33/48
[52] U.S. Cl. .................. 435/7.21; 435/7.23; 436/63; 436/64; 436/813
[58] Field of Search .................. 435/7.23, 7.4; 436/64, 813

[56] References Cited

U.S. PATENT DOCUMENTS

| | | | |
|---|---|---|---|
| 5,015,568 | 5/1991 | Tsujimoto et al. | 435/5 |
| 5,149,628 | 9/1992 | Croce | 435/6 |
| 5,198,338 | 3/1993 | Croce | 435/6 |
| 5,202,429 | 4/1993 | Tsujimoto et al. | 536/23.5 |
| 5,242,795 | 9/1993 | Croce | 435/6 |

OTHER PUBLICATIONS

Haldar et al, "Antiapoptosis potential of bcl–2 oncogene by dephosphorylation", Biochem. Cell. Biol., vol. 72, pp. 455–462, Oct. 2, 1994.

Allsopp, T. et al., "The Proto–Oncogene bcl–2 Can Selectively Rescue Neurotrophic Factor–Dependent Neurons from Apoptosis", Cell 1993, 73, 295–307.

Alnemri, E. et al., "Overexpressed Full–lenth Human BCL2 Extends the Survival of Baculovirus–infected Sf9 Insect Cells", PNAS USA 1992, 89, 7295–7299.

Alnemri, E. et al., "Involvement of BCL–2 in Glucocorticoid–induced Apoptosis of Human Pre–B–Leukemias", Cancer Research 1992, 52, 491–495.

Bissonnette, R. et al., "Apoptotic Cell Death Induced by c–myc is Inhibited by bcl–2", Nature 1992, 359, 552–554.

Boe, R. et al., "The Protein Phosphatase Inhibitor Okadaic Acid Induces Morphological Changes Typical of Apoptosis in Mammalian Cells", Experimental Cell Res.

Carson, D. et al., "Oral Antilymphocyte Activity and Induction of Apoptosis by 2–chloro–2'–arabino–fluoro–2'–deoxyadenosine", PNAS USA 1992, 89, 2970–2974.

Chen–Levy, Z. et al., "The bcl–2 Candidate Proto–Oncogene Product is a 24–Kilodalton Integral–Membrane Protein Highly Expressed in Lymphoid Cell LInes and Lymphomas Carrying the t(14;18) Translocation", Mol. and Cellular Biol. 1989, 9(2), 701–710.

Cohen, J. and Duke, "Apoptosis and Programmed Cell Death in Immunity", Annu. Rev. Immunol. 1992, 10, 267–93.

Cohen, P., "The Structure and Regulation of Protein Phosphates", Annu. Rev. Biochem. 1989, 58, 453–508.

Fernandez–Sarabia, M. and Bischoff, "Bcl–2 Associates with the ras–related Protein R–ras p23", Nature 1993, 366, 274–275.

Gaestel, M. et al., "Dephosphorylation of the Small Heat Shock Protein hsp25 by Calcium–Calmodulin–dependent (Type 2B) Protein Phosphatase", The J. of Biol. Chem.

Garcia, I. et al., "Prevention of Programmed Cell Death of Sympathetic Neurons by the bcl–2 Proto–Oncogene", Science 1992, 258, 302–304.

Gu, Y. et al., "The t(4;11) Chromosome Translocation of Human Acute Leukemias Fuses the ALL–1 Gene, Related to Drosophila trithorax, to the AF–4 Gene", Cell 1992, 71.

Haldar, S. et al., "Cellular Localization of the bcl–2 Protein and Response to Glucocorticoid Stress", Cell Death and Differentiation 1994, 1, 109–115.

Haldar, S. et al., "The bcl–2 Gene Encodes A Noel G Protein", Nature 1989, 342, 195–198.

Haldar, S. et al., "Down–regulation of bcl–2 by p53 in Breast Cancer Cells", Cancer Research 1994, 54, 2095–2097.

Haldar, S. et al., "Purification and Characterization of the bcl–2 Protein", Archives of Biochem. and Biophysics 1994, 315(2), 483–488.

Hengartner, M. and Horvitz, "Activation of C. elegans Cell Death Protein CED–9 by an Amino–acid Substitution in a Domain Conserved in Bcl–2", Nature 1994, 369, 318–.

Hockenbery, D. et al., "Bcl–2 Functions in an Antioxidant Pathway to Prevent Apoptosis", Cell 1993, 75, 241–251.

Hockenbery, D. et al., "Bcl–2 is an Inner Mitochondrial Membrane Protein that Blocks Programmed Cell Death", Nature 1990, 348, 334–336.

Krajewski, S. et al., "Investigation of the Subcellular Distribution of the bcl–2 Oncoprotein: Residence in the Nuclear Envelope, Endoplasmic Reticulum, and Outer".

Kyprianou, N. and Isaacs, "Thymineless Death in Androgen–independent Prostatic Cancer Cells", Biochem. and Biophys. Res. Comm. 1989, 165(1), 73–81.

McDonnell, T. et al., "bcl–2–Immunoglobulin Transgenic Mice Demonstrate Extended B Cell Survival and Follicular Lymphoproliferation", Cell 1989, 57, 79–88.

(List continued on next page.)

Primary Examiner—Lila Feisee
Assistant Examiner—Yvnne Eyler
Attorney, Agent, or Firm—Woodcock Washburn Kurtz Mackiewicz & Norris, LLP

[57] ABSTRACT

Methods of identifying compounds that modulate bcl-2 mediated cell death are disclosed. The methods comprise contacting a cell or cell extract with a test compound and detecting the level of bcl-2 phosphorylation compared to the level of bcl-2 phosphorylation in a similar cell or cell extract not contacted with the test compound. Methods of treating an individual susceptible to or suffering from a disease characterized by inhibition of apoptosis are disclosed. The methods comprise administering to such an individual an bcl-2 phosphorylation compound that inhibits dephosphorylation of bcl-2 and/or facilitates phosphorylation of bcl-2. Methods of treating an individual susceptible to or suffering from a diseases characterized by apoptosis are disclosed. The methods comprise administering to such an individual a bcl-2 dephosphorylation compound that inhibits phosphorylation of bcl-2 and/or facilitates dephosphorylation of bcl-2.

13 Claims, No Drawings

OTHER PUBLICATIONS

Miyashita, T. and Reed, "bcl–2 Gene Transfer Increases Relative Resistance of S49.1 and WEHI7.2 Lymphoid Cells to Cell Death and DNA Fragmentation Induced by Glucocorticoids and Multiple Chemotherapeutic Drugs", *Cancer Research* 1992, 52, 5407–5411.

Negrini, M. et al., "Molecular Analysis of mbcl–2: Structure and Expression of the Murine Gene Homologous to the Human Gene Involved in Follicular Lymphoma", *Cell*.

Oltvai, Z.N. et al., "Bcl–2 Heterodimerizes In vivo with a Conserved Homolog, Bax, That Accelerates Programmed Cell Death", *Cell* 1993, 74, 609–619.

Reed, J., "Bcl–2 and the Regulation of Programmed Cell Death", *The J. of Cell Biol.* 1994, 124(1,2), 1–6.

Schwartzman, R. and Cidlowski, "Apoptosis: The Biochemistry and Molecular Biology of Programmed Cell Death", *Endocrine Reviews* 1993, 14(2), 133–151.

Somers, J. and DeFranco, "Effects of Okadaic Acid, a Protein Phosphatase Inhibitor, on Glucocorticoid Receptor–Mediated Enhancement", *Molecular Endocrinology*.

Strasser, A. et al., "bcl–2 Transgene Inhibits T Cell Death and Perturbs Thymic Self–censorship", *Cell* 1991, 67, 889–899.

Tsujimoto, Y. et al., "Cloning of the Chromosome Breakpoint of Neoplastic B Cells with the t(14;18) Chromosome Translocation", *Science* 1984, 226, 1097–1099.

Tsujimoto, Y. et al., "Involvement of the bcl–2 Gene in Human Follicular Lymphoma", *Science* 1985, 228, 1440–1443.

Wyllie, A.H., "Glucocorticoid–induced Thymocyte Apoptosis is Associated with Endogenous Endonuclease Activation", *Nature* 1980, 284, 555–556.

Yin, X. et al., "BH1 and BH2 Domains of Bcl–2 Are Required for Inhibition of Apoptosis and Heterodimerization with Bax", *Nature* 1994, 369, 321–323.

Bonnefoy–Berard, et al., "Calcineurin and Kinases in the Control of BCL–2 Expression and Apoptosis in Human B Cell Lines", *J. Immunol.*, 150, No. 8, part 2, issued 25, May, 1993, p. 186A, Col. 2, Abstract No. 1056.

Haldar, et al., "Inactivation of BCL–2 by Phosphorylation", *Proc. Natl. Acad. Sci. USA*, 92, No. 10, issued May 9, 1995, pp. 4507–4511.

MODULATION OF BCL-2 PHOSPHORYLATION

FIELD OF THE INVENTION

The invention relates to identifying compounds that modulate the phosphorylation of the bcl-2.

BACKGROUND OF THE INVENTION

Apoptosis is a widespread process involving chromatin cleavage at 180–200 base pair intervals, nuclear condensation, cellular fragmentation and phagocytosis (Wyllie, A. H. (1980) Nature 284:555–556). It may be activated by a wide range of hormones, growth factors and cytokines (Schwartzaman, R. A. and Cidlowski, J. A. (1993) Endocrine Rev 14:133–151). Apoptosis is often the process by which HIV infected T cells are destroyed. There is growing evidence that the efficacy of certain anti-cancer agents is related to the intrinsic propensity of target cells to respond to these compounds by apoptosis (Carson, D.A., et al. (1992) Proc. Natl. Acad. Sci. USA 89:2970–2974; Kyprianou, N. and Isaacs, J. T. (1989) Biochem. Biophys. Res. Commum. 165:73–81; and Bhalla, K., et al. (1993) Leukemia 7:563–565).

Bcl-2 is a 26 kilodalton integral membrane oncoprotein which is unique in its ability to suppress apoptosis (Tsujimoto, Y., et al. (1984) Science 226:1097–1099). Overexpression of p26 bcl-2 is responsible for follicular lymphoma and is caused by the juxtaposition of the bcl-2 gene to immunoglobulin heavy chain enhancer elements (Tsusimoto,Y., et al. (1985) Science 228:1140–1443; and Tsujimoto, Y., et al. (1984) Science 226:1097–1099) arising from a t(14;18) chromosomal translocation. The t(14;18) translocation deregulates bcl-2 expression by placing it under the control of IgG gene regulatory elements. Deregulated bcl-2 expression confers interleukin independent survival where the lifespan of precancerous B cells is extended to facilitate malignant transformation. Numerous studies have examined the consequences of bcl-2 over expression in stable transfected cell lines, transgenic mice, and antisense deletion, with the common outcome being altered cell survival. The global nature of this response is especially striking as the diversity of apoptotic stimuli which are blocked by bcl-2 including radiation, growth factor withdrawal, glucocorticoids and multiple chemotherapeutic agents (McDonnell, T. J., et al. (1989) Cell 57:79–88; Bissonnette, R. P., et al. (1992) Nature 359:552–553; Garcia, I., et al. (1992) Science 258:302–304; and Miyashita, T. and Reed, J. C. (1992) Cancer Res. 52:5407–5411).

Early studies attributed the anti-apoptosis function of bcl-2 to mitochondrial energy metabolism (Hockenberry, D., et al. (1990) Nature 348:334–336), however, the p26-bcl-2 oncoprotein has widespread subcellular localization in membranes including the nuclear envelope (Chen-Levy, Z., et al. (1989) Mol. Cell. Biol. 9:701–710; Krajewski, S., et al. (1993) Cancer Res. 53:4701–4714; Monaghan, P., et al. (1992) J. Histochem. Cytochem. 40:1819–1825; and Haldar, S., et al. (1994) Cell Death & Differentiation 1:109–115). Bcl-2 may, however, be important in maintaining membrane lipid integrity by suppressing the generation of reactive oxygen species (Hockenberry, D. M., et al. (1993) Cell 75:214–251). Some indications are that bcl-2 dimerizes with itself or a related 21 KDa protein, BAX, (bcl-2 associated protein), where bcl-2 heterodimer with BAX promotes cell survival, whence BAX/BAX homodimer predisposes to apoptosis (Oltvai, Z. N., et al. (1993) Cell 75:609–619).

It is known that glucocorticoid induced apoptosis of immature lymphocytes can be prevented by expression of bcl-2 in the lymphoid cells (Alnemri, E. S., et al. (1992) Cancer Res. 52:491–495; Allsopp, T. E., et al. (1993) Cell 73:295–307; Strasser, A., et al. (1991) Cell 67:889–899). Recently, the effects of okadaic acid (OA), a protein phosphatase inhibitor, on glucocorticoid receptor-mediated transcriptional enhancement has been described. Morphological changes typical of apoptosis were also observed in mammalian cells following treatment with this protein phosphatase inhibitor (Boe, R., et al. (1991) Exp. Cell Res. 195:237–246).

There is a need to identify compounds which modulate bcl-2's ability to alter cell survival. There is a need to identify compounds which modulate the ability of bcl-2 to prevent apoptosis. There is a need to identify compounds which can affect bcl-2 to induce apoptosis.

SUMMARY OF THE INVENTION

The invention relates to methods of identifying compounds that modulate bcl-2 mediated cell death. The methods comprise the steps of contacting a cell with a test compound and then detecting whether bcl-2 in the cell is phosphorylated at a different level than it is in a similar cell that is not contacted with the test compound. Phosphorylation of bcl-2 at a higher level in the cell contacted with the test compound indicates that the test compound modulates cell death by inducing cell death. Phosphorylation of bcl-2 at a lower level in the cell contacted with the test compound indicates that the test compound modulates cell death by preventing apoptosis.

The invention relates to methods of identifying compounds that modulate bcl-2 mediated cell death. The methods comprise the steps of generating cell extracts that include bcl-2, contacting the cell extract with a test compound and then detecting whether bcl-2 in the cell extract is phosphorylated at a different level than it is in a similar cell extract that is not contacted with the test compound. Phosphorylation of bcl-2 at a higher level in the cell extract that is contacted with the test compound indicates that the test compound modulates cell death by inducing cell death. Phosphorylation of bcl-2 at a lower level in the cell extract that is contacted with the test compound indicates that the test compound modulates cell death by preventing apoptosis.

The invention relates to a method of treating an individual susceptible to or suffering from a disease(s) characterized by transformed cells that overexpress bcl-2. The methods comprise the steps of identifying such an individual and then administering to the individual an amount of a bcl-2 phosphorylation compound that is sufficient to inhibit dephosphorylation of bcl-2 and/or facilitate phosphorylation of bcl-2.

The invention relates to a method of treating an individual susceptible to or suffering from a diseases characterized by apoptosis. The methods comprise the steps of identifying such an individual and then administering to the individual an amount of a bcl-2 dephosphorylation compound that is sufficient to inhibit phosphorylation of bcl-2 and/or facilitate dephosphorylation of bcl-2.

DETAILED DESCRIPTION OF THE INVENTION

It has been discovered that bcl-2 loses its anti-apoptosis potential following serine phosphorylation. It has been discovered that phosphorylation of the bcl-2 product leads to induction of apoptosis. Thus, dephosphorylation of bcl-2 could be a molecular determinant of cell survival. A protein called R-ras p23 has been found to be associated with bcl-2. It is known that overexpression of R-ras p23 cannot transform cells but can induce apoptosis. Since Ras p23 acts upstream of Raf-1 kinase, activation of Raf-1 kinase pathway may lead to phosphorylation of bcl-2 leading to inactivation of bcl-2 and cell death.

Bcl-2 phosphorylation is induced at high concentration of okadaic acid, a characteristic of Group 2B phosphatases. Moreover, calyculin A or microcystin LR, inhibitors of Group I and 2A phosphatases does not effect bcl-2 phosphorylation. In addition, calcineurin, a $Ca^{++}$ and calmodulin dependent phosphatase can dephosphorylate phosphorylated bcl-2. These data, cumulatively, indicate that bcl-2 may be regulated by a Group 2B phosphatase, which is calcium and calmodulin dependent.

The discovery that the phosphorylation of the bcl-2 product leads to induction of apoptosis and that the dephosphorylation of bcl-2 produces an anti-apoptotic effect allows for the use of compounds that phosphorylate or dephosphorylate bcl-2 as modulators of cell death. Further, the discovery provides the basis for methods of identifying compounds that modulate cell death.

According to some embodiments of the invention, compounds that are inhibitors of Group 2B phosphatases are administered to individuals suffering from diseases associated with hypophosphorylated bcl-2. The present invention relates to methods of treating individuals who have such diseases by administering a therapeutically effective amount of a compound that inhibits Group 2B phosphotases and/or enhances bcl-2 phosphorylation.

The means to identify individuals suffering from diseases associated with bcl-2 are well known and described in U.S. Pat. No. 5,015,568 issued May 14, 1991, which is incorporated herein by reference. As described herein, it has now been discovered that phosphorylation of bcl-2 eliminates its anti-apoptotic effects. Therefore, individuals who have been identified as having neoplasms associated with bcl-2 overexpression may be treated with compounds that will lead to the phosphorylation of bcl-2, inactivate its anti-apoptotic effects, and thereby lead to the death of the cancer cells. Compounds that will lead to the phosphorylation of bcl-2 include compounds which inhibit Group 2B phosphatases, which are shown herein to dephosphorylate bcl-2. In addition, compounds which enhance phosphorylation by upregulating kinase activity associated with bcl-2 phosphorylation will also be useful to reduce the anti-apoptotic effects of bcl-2 in cancer cells.

According to some embodiments of the invention, compounds that enhance Group 2B phosphatase activity are administered to individuals suffering from diseases, disorders or conditions characterized by apoptosis, such as for example Alzheimer's disease. The present invention relates to methods of treating individuals who have diseases, disorders or conditions characterized by apoptosis by administering a therapeutically effective amount of a compound that enhances the activity of Group 2B phosphotases and/or inhibits bcl-2 phosphorylation.

In individuals suffering from HIV infection, a clinical manifestation of AIDS is a severe reduction in the number of T cells. While T cells are a primary host cell for HIV infection and replication, it is believed that one of the mechanisms by which T cells die is apoptosis. As described herein, it has now been discovered that phosphorylated bcl-2 is apoptotic while dephosphorylated bcl-2 is anti-apoptotic. That is, phosphorylated bcl-2 does not prevent apoptosis while dephosphorylated bcl-2 prevents apoptosis. Thus, individuals who have diseases, disorders or conditions associated with undesirable cell death due to apoptosis may be treated by administering compounds that prevent apoptosis by either enhancing dephosphorylation of bcl-2 or inhibiting phosphorylation of bcl-2. Accordingly, compounds that enhance phosphatase activity or inhibit kinase activity are useful to prevent apoptosis.

According to some embodiments of the invention, test compounds may be screened and compounds identified that inhibit dephosphorylation of bcl-2. Such compounds may be inhibitors of Group 2B phosphatases. Such methods are useful to identify compounds which may be useful as anti-cancer drugs.

According to some embodiments of the invention, test compounds may be screened and compounds identified that enhance phosphorylation of bcl-2. Such compounds may increase the activity of the kinase that phosphorylates bcl-2. Such methods are useful to identify compounds which may be useful as anti-cancer drugs.

According to some embodiments of the invention, test compounds may be screened and compounds identified that enhance dephosphorylation of bcl-2. Such compounds may increase Group 2B phosphatase activity. Such methods are useful to identify compounds which may be useful as drugs to treat diseases characterized by apoptosis, such as for example Alzheimer's disease.

According to some embodiments of the invention, test compounds may be screened and compounds identified that inhibit phosphorylation of bcl-2. Such compounds may inhibit the kinase that phosphorylates bcl-2. Such methods are useful to identify compounds which may be useful as drugs to treat diseases characterized by apoptosis, such as for example Alzheimer's disease.

Assays can be performed to identify compounds that effect phosphorylation of bcl-2. Specifically, assays can be performed to identify compounds that increase the phosphorylation of bcl-2 or assays can be performed to identify compounds that decrease the phosphorylation of bcl-2. Assays may be performed on cells or cell extracts.

In assays that use cells, the cells are contacted with test compounds. In some embodiments, after incubating the cells with the test compound for an amount of time sufficient to effect the phosphorylation and dephosphorylation of bcl-2 in the cell, the cells are lysed and the amount of phosphorylated bcl-2 and/or dephosphorylated bcl-2 present in the cells is compared to identical cells that were not exposed to test compound. In some embodiments, Western blot technology is used with the cell proteins separated by electrophoresis and antibodies that bind to bcl-2. Alternatively, the cells may be incubated in the presence of radiolabelled phosphorus that is then used to detect whether the bcl-2 is phosphorylated or unphosphorylated. In some embodiments, after incubating the cells with the test compound for an amount of time sufficient to effect the phosphorylation and dephosphorylation of bcl-2 in the cell, the cells are analyzed to determine whether the occurrence and extent of apoptosis. Cells may be analyzed by the detection of chromosomal DNA fragmentation.

In some embodiments, cells are treated in vitro with test compounds at 37° C. in a 5% $C_2$ humidified atmosphere. Following treatment with test compounds, cells are washed with $Ca^{2+}$ and $Mg^{2+}$ free PBS and total protein is extracted as described (Haldar, S., et al. (1994) Cell Death & Differentiation 1:109–115; Haldar, S., et al. (1989) Nature 342:195–198; Haldar, S., et al. (1994) Cancer Res. 54:2095–2097, which are incorporated herein by reference.

In some embodiments, bcl-2 phosphorylation is analyzed using Western blotting and immunodetection which are performed using Amersham ECL detection system and well known methodology.

Phosphorylation of lymphoid cells may be carried out in phosphate free media (GIBCO) using 1 mCi/ml [$p^{32}$] orthophosphoric acid (NEN) for 6 hrs in the presence of a test compound. In some embodiments, serial dilutions of test compound are used. Immunoprecipitation of $P^{32}$ labeled cellular extract is essentially done by the described in Haldar, S. et al. (1989) Nature 342:195–198. Immunocomplex is run on a 0.75 mm thick 10% SDS-PAGE. Subsequently, gels are dried and exposed for autoradiography using Kodak XAR films.

Phospho-amino acid analysis is performed essentially as described in the manual for the Hunter thin layer electrophoresis system, HTLE700, (CBS Scientific Company Inc., USA). Briefly, $p^{32}$ labelled immunoprecipitates are run on 10% SDS-PAGE gels. The bcl-2 immunoreactive bands are cut out of the gel and eluted with 50 µM ammonium bicarbonate. After elution, the proteins are precipitated in the presence of 15% –20% TCA plus carrier protein, and washed with ethanol. Precipitated protein is then oxidized in performic acid and lyophilized. The dried pellet is resuspended in constant boiling HCl heated at 110° C. and lyophilized; the residue is resuspended in pH 1.9 buffer (50 ml formic acid, 156 ml acetic acid, 1794 ml $H_2O$) containing phospho-amino acid standards and spotted on a PEI cellulose plate. Two dimensional thin layer chromatography is run using the pH 1.9 buffer for the first dimension and pH 3.5 buffer (100 ml acetic acid, 10 ml pyridine, 1890 ml $H_2O$) for the second. The plate is baked at 65° C. for 10 min, and the cold standards are visualized by spraying the plate with 0.25% ninhydrin and returning the plate to the 65° C. oven for 15 min. The plate is then exposed with Kodak X-omat AR film for two to four weeks.

Following treatment with test compounds, cells are washed with PBS and loaded with 5 µM Cis-parinaric acid for 1 hr at 37° C. Subsequently, cis-parinaric acid loaded cells are washed and suspended in complete medium. Cells are then challenged with 1 µM dexamethasone. Immediately after the addition of dexamethasone, fluorescence measurements are made on a fluorescence activated cell sorter (Elite) equipped with a 37° C. sample chamber at an excitation wavelength of 334–364 nm and emission wavelength of 450 nm. Gating is performed to remove dead cells prior to data collection.

Morphologically, changes characteristic of apoptosis may be monitored by staining cell nuclei with DAPI (Boehringer-Mannheim, Indiana) which preferentially stains adenine-and thymine-rich DNA. Lymphoid cells treated with test compounds are grown on poly-L-lysine coated coverslips. After processing, the cells are fixed using 4% formalin. Following washes, the cells are permeabilized using 0.1% Triton-X-100. Permeabilized cells are stained with DAP-I staining solution (2 mg/ml) for 30 secs. at room temperature. After brief washes, coverslips are mounted using gelvatol/glycerol based mounting media. Nuclear fragmentation is examined under UV (370 nm) light for blue nuclear DAPI staining using Leitz fluorescence microscope.

The diphenylamine assay for determining DNA fragmentation is carried out as follows. $2 \times 10^8$ cells are contacted with test compounds and lysed with extraction buffer containing 50 mM Tris pH 8.0, 20 mM EDTA and 0.5% Triton X-100 for 30 min at 4° C. Lysed cells are centrifuged at 21000x g at 4° C. DNA is precipitated from the supernatant and the pellet in 1N perchloric acid. DNA content in the supernatant and pellet is determined by incubating DNA solution with diphenylamine reagent for 18 hr. Following colorimetric reactions, readings are taken on a Perkin Elmer uv/vis lambda-2 Spectrophotometer at 600 nm. Diphenylamine reagent is prepared by dissolving 1.5 g of steam distilled diphenylamine (Aldrich Chemical Co., USA) in 100 ml of redistilled acetic acid and 1.5 ml of conc. sulfuric acid. The reagent is stored in the dark. 0.1 ml of aqueous acetaldehyde is added to 20 ml of diphenylamine reagent before starting the reaction with DNA.

In some embodiments, modulation of bcl-2 phosphorylation is analyzed using cell extract material as a starting material. Test compounds are combined with cell extract material and the effect of the compounds on bcl-2 phosphorylation is examined. In some embodiments, the cell extract material is contacted with test compounds to identify the effect of the test compound on dephosphorylation. In some embodiments, bcl-2 is phosphorylated with radiolabelled $^{32}P$ and the cell extract material is contacted with test compounds to identify the effect the test compound has on dephosphorylation. In some embodiments, the cell extract material is contacted with test compounds to identify the effect the test compound has on phosphorylation of bcl-2. In some embodiments, the cell extract material is contacted with test compounds in the presence of $^{32}P$ to identify the effect the test compound has on phosphorylation of bcl-2.

Cell extract is treated in vitro at 37° C. using 100 µg total cellular extract with specified concentration of test compounds. For phosphatase reactions, 50 µl cell lysate is contacted with test compound and incubated with a reaction mixture containing 1U/µl calcineurin (Calbiochem), and 0.5 unit/µl Calmodulin (Calbiochem) for 30–60 mins. at 370° C.

For phosphorylation and dephosphorylation of cell extract material, 100 µg cellular extract is treated as described above except 40 µci [$\tau$-$^{32}P$] ATP (3000 Ci/mmol) are added to each reaction. Reactions are stopped by immersing the tubes in ice. The [$\tau$-$^{32}P$] ATP labeled reaction mixture is absorbed on immunoaffinity column made from the monoclonal antibody against bcl-2 by covalently binding purified antibodies to protein-A Sepharose using the crosslinker dimethylpimelimidate dihydrochloride (50 mM). Specifically bound [$\tau$-$^{32}P$] ATP labeled bcl-2 protein is eluted with 0.05M diethylamine, pH 11.5 containing 0.5% Na-deoxycholate.

Western blotting and immunodetection is done using Amersham ECL detection system and well known methodology. Immunoprecipitation of $p^{32}$ labeled cellular extract was essentially done by the method described in Haldar, S. et al. (1989) Nature 342:195–198. Immunocomplex was run on a 0.75 mm thick 10% SDS-PAGE. Subsequently, gels were dried and exposed for autoradiography using Kodak XAR films.

Phosphoaminoacid analysis was performed essentially as described in the manual for the Hunter thin layer electrophoresis system, HTLE700, (CBS Scientific Company Inc., USA). Briefly, $P^{32}$ labelled immunoprecipitates were run on 10% SDS-PAGE gels. The bcl-2 immunoreactive bands were cut out of the gel and eluted with 50 µM ammonium bicarbonate. After elution the proteins were precipitated in the presence of 15% –20% TCA plus carrier protein, and washed with ethanol. Precipitated protein was then oxidized in performic acid and lyophilized. The dried pellet was resuspended in constant boiling HCl heated at 110° C. and lyophilized; the residue was resuspended in pH 1.9 buffer (50 ml formic acid, 156 ml acetic acid, 1794 ml $H_2O$) containing phospho-amino acid standards and spotted on a PEI cellulose plate. Two dimensional thin layer chromatography was run using the pH 1.9 buffer for the first dimension and pH 3.5 buffer (100 ml acetic acid, 10 ml pyridine, 1890 ml H$_2$O) for the second. The plate was baked at 65° C. for 10 min, and the cold standards were visualized by spraying the plate with 0.25% ninhydrin and returning the plate to the 65° C. oven for 15 min. The plate was then exposed with Kodak X-omat AR film for two to four weeks.

EXAMPLE

MATERIALS AND METHODS

Cell and cell extract treatment with phosphatase inhibitors or drugs

Cells were treated in vitro with phosphatase inhibitors at 37° C. in a 5% CO$_2$ humidified atmosphere. Following treatment with DMSO or phosphatase inhibitors, cells were washed with Ca$^{2+}$ and Mg$^{2+}$ free PBS and total protein was extracted as described (Haldar, S., et al. (1994) *Cell Death & Differentiation* 1:109–115; Haldar, S., et al. (1989) *Nature* 342:195–198; Haldar, S., et al. (1994) *Cancer Res.* 54:2095–2097, which are incorporated herein by reference.

Cells were treated in vitro with taxol was basically the same as OA, except the time of treatment was 24 hrs.

Cell extract was treated in vitro at 37° C. using 100 μg total cellular extract with specified concentration of phosphatase inhibitors. For phosphatase reactions, 50 μl DMSO or OA treated cell lysate were incubated with a reaction mixture containing 1U/μl calcineurin (Calbiochem), and 0.5 unit/μl Calmodulin (Calbiochem) for 30-60 mins. at 37° C.
Immunoblotting Western blotting and immunodetection was done using Amersham ECL detection system using well known methodology.
Two dimensional Phospho-amino acid analysis Phosphorylation of lymphoid cells was carried out in phosphate free media (GIBCO) using 1 mCi/ml [p$^{32}$] orthophosphoric acid (NEN) for 6 hrs in the presence of DMSO or 1 μM OA. Immunoprecipitation of P$^{32}$ labeled cellular extract was essentially done by the described in Haldar, S. et al. (1989) *Nature* 342:195–198. Immunocomplex was run on a 0.75 mm thick 10% SDS-PAGE. Subsequently, gels were dried and exposed for autoradiography using Kodak XAR films.

Phospho-amino acid analysis was performed essentially as described in the manual for the Hunter thin layer electrophoresis system, HTLE700, (CBS Scientific Company Inc., USA). Briefly, P$^{32}$ labelled immunoprecipitates were run on 10% SDS-PAGE gels. The bcl-2 immunoreactive bands were cut out of the gel and eluted with 50 μM ammonium bicarbonate. After elution the proteins were precipitated in the presence of 15% –20% TCA plus carrier protein, and washed with ethanol. Precipitated protein was then oxidized in performic acid and lyophilized. The dried pellet was resuspended in constant boiling HCl heated at 110° C. and lyophilized; the residue was resuspended in pH 1.9 buffer (50 ml formic acid, 156 ml acetic acid, 1794 ml H$_2$O) containing phospho-amino acid standards and spotted on a PEI cellulose plate. Two dimensional thin layer chromatography was run using the pH 1.9 buffer for the first dimension and pH 3.5 buffer (100 ml acetic acid, 10 ml pyridine, 1890 ml H$_2$O) for the second. The plate was baked at 65° C. for 10 min, and the cold standards were visualized by spraying the plate with 0.25% ninhydrin and returning the plate to the 65° C. oven for 15 min. The plate was then exposed with Kodak X-omat AR film for two to four weeks.

Phosphorylation and dephosphorylation of cell extract material

For phosphorylation and dephosphorylation of cell extract material, 100 μg cellular extract was treated as described above except 40 μci [τ-$^{32}$P] ATP (3000 Ci/mmol) were added to each reaction. Reactions were stopped by immersing the tubes in ice. The [τ-$^{32}$P] ATP labeled reaction mixture was absorbed on immunoaffinity column made from the monoclonal antibody against bcl-2 by covalently binding purified antibodies to protein-A Sepharose using the crosslinker dimethylpimelimidate dihydrochloride (50 mM). Specifically bound [τ-$^{32}$P] ATP labeled bcl-2 protein was eluted with 0.05M diethylamine, pH 11.5 containing 0.5% Na-deoxycholate.
Lipid peroxidation assay using florescent cis-parinaric acid Following treatment with OA or DMSO, cells were washed with PBS and loaded with 5 μM Cis-parinaric acid for 1 hr at 37° C. Subsequently, cis-parinaric acid loaded cells were washed and suspended in complete medium. Cells were then challenged with 1 μM dexamethasone. Immediately after the addition of dexamethasone, fluorescence measurements were made on a fluorescence activated cell sorter (Elite) equipped with a 37° C. sampler chamber at an excitation wavelength of 334–364 nm and emission wavelength of 450 nm. Gating was performed to remove dead cells prior to data collection.
Morphological determination of apoptotic nuclei Morphologically, changes characteristic of apoptosis were monitored by staining cell nuclei with DAPI (Boehringer-Mannheim, Indiana) which preferentially stains adenine-and thymine-rich DNA. Taxol or okadaic acid treated lymphoid cells were grown on poly-L-lysine coated coverslips. After processing, the cells were fixed using 4% formalin. Following washes, the cells were permeabilized using 0.1% Triton-X-100. Permeabilized cells were stained with DAP-I staining solution (2mg/ml) for 30 secs. at room temperature. After brief washes, coverslips were mounted using gelvatol/glycerol based mounting media. Nuclear fragmentation was examined under UV (370 nm) light for blue nuclear DAPI staining using Leitz fluorescence microscope.
Diphenylamine assay for measuring DNA fragmentation The diphenylamine assay for determining DNA fragmentation was carried out as follows. 2×10$^8$ DMSO or OA treated cells were lysed with extraction buffer containing 50 mM Tris pH 8.0, 20 mM EDTA and 0.5% Triton X-100 for 30 min at 4° C. Lysed cells were centrifuged at 21000×g at 4° C. DNA was precipitated from the supernatant and the pellet in 1N perchloric acid. DNA content in the supernatant and pellet was determined by incubating DNA solution with diphenylamine reagent for 18 hr. Following colorimetric reactions, readings were taken on a Perkin Elmer uv/vis lambda-2 Spectrophotometer at 600 nm. Diphenylamine reagent was prepared by dissolving 1.5 g of steam distilled diphenylamine (Aldrich Chemical Co., USA) in 100 ml of redistilled acetic acid and 1.5 ml of conc. sulfuric acid. The reagent was stored in the dark. 0.1 ml of aqueous acetaldehyde was added to 20 ml of diphenylamine reagent before starting the reaction with DNA.

RESULTS AND DISCUSSION

Lymphoid cells overexpressing bcl-2 were treated with several phosphatase inhibitors e.g. okadaic acid, calyculin A or microcystin LR. Of these three phosphatase inhibitors, only okadaic acid can induce modification of bcl-2 infected Sf9 insect cells. 1 μM okadaic acid treatment for 2–24 hrs results in accumulations of modified bcl-2. 10-20 nM CalyculinA or 1 µM microcystin LR (other phosphatase inhibitors) did not demonstrate any effect in vivo. The absence of effect of microcystin LR or calyculin A on the modification of bcl-2 protein could be due to the differences in the cell permeability of these agents. To address this question, vitro experiments using these phosphatase inhibitors were also undertaken. In vitro, okadaic acid (500 nM-1 µM) was able to induce modified bands of bcl-2 whereas calyculin A or microcystin LR did not induce modification of bcl-2 protein in several lymphoid cell lines tested in vitro.

In vivo, okadaic acid did not induce any modification of bcl-2 protein at a concentration less than 800 nM. To determine if the altered mobility of modified bcl-2 was due to phosphorylation, in vitro experiments were carried out using phosphatases in the incubation mixture. Calcineurin, a $Ca^{++}$ and calmodulin dependent phosphatase, can abolish the appearance of modified bcl-2 protein, whereas potato acid phosphatase was without effect. The mobility change in bcl-2 may be due to phosphorylation of a portion of the protein.

Since, several chemotherapeutic agents such as taxol or 5' fluorouracil are known to induce apoptosis in leukemia cells, lymphocytes expressing bcl-2 were treated with taxol or 5' fluorouracil for several time periods. These drugs can also induce phosphorylation of bcl-2, with the onset of apoptosis.

In order to determine if immunoprecipitation of bcl-2 would also allow observations of the modified bcl-2 protein, specifically immunoprecipitated bcl-2 protein from several lymphoid cell lines treated with okadaic acid or taxol were transferred to nitrocellulose and the protein was detected on the western blot using the same bcl-2 antibody; indeed, a similar pattern of modification was observed in OA or taxol treated lymphocytes. Moreover, two proB cell lines MV (4:11) and RS (4:11) derived from acute lymphoblastic leukemias (ALL) exhibiting the (4;11) chromosomal translocation (Gu, Y. et al. (1992) Cell 71:701–708.) were subjected to immunoblotting using specific monoclonal antibody against bcl-2. These two cell lines exhibited modified bcl-2 protein without okadaic acid treatment. These leukemic cell lines exhibit a large fraction of apoptotic cells when compared to pre-B cell lines or a lymphoblastoid B cell line, as shown by DNA fragmentation.

In vivo [$^{32}$P] labeled cellular proteins were immunoprecipitated with antibody against bcl-2 in the presence or absence of okadaic acid. In the absence of okadaic acid, it is difficult to detect bcl-2 phosphorylation, except in RS (4:11) and MV (4:11) cells. Both RS (4:11) and MV (4:11) cells were found to constitutively express phosphorylated bcl-2 protein when [$^{32}$P] labeled cellular extract from these cell lines was immunoprecipitated with antibody against bcl-2 protein. In presence of okadaic acid, bcl-2 is phosphorylated in all lymphoid cell lines tested except the B lymphoblastoid cell line GM1500. Another ~35 kDa phosphoprotein was also co-immunoprecipitated with bcl-2.

The phosphorylated bcl-2 band was excised from the dried gel, digested and phospho-amino acid analysis was carried out using two dimensional thin layer chromatography. Results indicated that bcl-2 is phosphorylated at serine residue(s). The other phosphorylated 35 kDa protein band, which co-immunoprecipitated with bcl-2 protein, was found to be phosphorylated on both serine and tyrosine residues.

Similar results were also observed when cells were exposed to taxol treatment for 24 hrs and [$^{32}$p] orthophosphoric acid was added for last 6 hrs of treatment. After taxol treatment, bcl-2 was also found to be phosphorylated at serine residue(s).

Calcineurin, a Ca++ and calmodulin dependent phosphatase but not the other phosphatase such as acid phosphatase can abolish the altered mobility of the bcl-2 protein in vitro. Likewise, to determine if in vitro [$^{32}$P] labeled bcl-2 protein is dephosphorylated by calcineurin, phosphorylation of cellular extract from lymphoid cells using [τ-32p] ATP was carried out in absence or presence of OA. Next, dephosphorylation reaction was performed using calcineurin and phosphorylated cellular extract at 37° C. for 1 hr. Both calcineurin treated and untreated reaction mixture were absorbed on immunoaffinity columns (Haldar, S. et al. (1994) Arch. Biochem. Biophys. 315:483–488) and immunoprecipitated [τ-32p] ATP labeled bcl-2 protein was run on a SDS-PAGE. Autoradiography of the dried gel indicates that in the presence of OA, bcl-2 protein is phosphorylated whereas a calmodulin dependent phosphatase, calcineurin, dephosphorylates it.

To determine if there is a correlation between phosphorylation of bcl-2 and its function, bcl-2 expressing cells were treated with 1 µM okadaic acid for 4 hrs at 37° C. and a portion of cells were stained with nuclear specific stain 4'6'-diamidino-2-phenylindole (DAPI) to detect changes in the morphology of nuclei. The hallmark of apoptosis is the collapse of the nucleus, while other organelles are relatively well maintained. Chromatin becomes extremely condensed and tends to marginate in crescents around the nuclear envelope; in many cell types it collapses into the densest possible form, one or several spheres. In most lymphoid cell lines tested, apoptosis was detected following OA treatment as evidenced by nuclear morphology change. Overexpression of bcl-2 could not prevent the OA or taxol induced apoptosis, presumably caused by phosphorylation of the bcl-2 protein. Epstein-Barr virus immortalized lymphoblastoid B cell line GM1500 did not undergo apoptosis, as measured by lack of changes in nuclear morphology following OA exposure. OA treated GM1500 cellular extract was analyzed for the presence of phosphorylated bcl-2 protein. Strikingly, modified bcl-2 protein was not detected following OA treatment. It is not clear why OA or taxol does not induce phosphorylation of bcl-2 and programmed cell death in bcl-2 expressing GM1500 cells. The above experiments established a correlation between phosphorylation bcl-2 and induction of apoptosis.

In addition, the extent of apoptosis was determined in several lymphoid cell lines following OA exposure. By diphenylamine assay a significant increase in DNA fragmentation in okadaic acid treated lymphoid cells was detected except in lymphoblastoid B cells, GM1500. Similar increase in DNA fragmentation was observed when 697 and 12B2 cells were treated with 1 µM taxol for 24 hrs.

In order to determine whether phosphorylated bcl-2 can function in an antioxidant pathway to prevent apoptosis, lipid peroxidation was investigated using fluorescent cis-parinaric acid. Lymphoid cells were treated with DMSO or 1 µM okadaic acid for 4 hrs at 37° C. Following treatment, cells were washed and loaded with 5 µM cis-parinaric acid (Molecular Probes, Eugene, USA) for 1 hr at 37° C. Cis-parinaric acid loaded cells were washed and resuspended in complete growth medium. Control cells (no treatment), DMSO and OA treated cells were then subjected to 1 µM dexamethasone treatment for 16 hrs. Fluorescence was measured immediately following dexamethasone addition and after 16 hrs treatment for each group of cells. 697 cells, which do not express sufficient bcl-2 to resist glucocorticoid induced apoptosis, are also unable to prevent lipid peroxidation as evidenced by flow cytometry quantitation of cis-parinaric acid fluorescence. In contrast, 12B2 cells (697 cells engineered to overexpress bcl-2) can resist dexamethasone induced apoptosis by preventing lipid peroxidation. This is not surprising since overexpression of bcl-2 can protect cells from apoptotic cell death by blocking lipid peroxidation. Following OA treatment, bcl-2 can no longer prevent lipid peroxidation as evidenced by decrease in cis-parinaric acid fluorescence.

Although the evidence indicates that bcl-2 is inactivated by phosphorylation, it is possible that the phosphorylation of other proteins is associated with apoptosis. Since okadaic acid can induce phosphorylation of many proteins, p53, another protein involved in apoptosis, was studied to determine if it would be phosphorylated under similar conditions. No modification of p53 protein was observed by immunoblotting and immunodetection using p53 specific antibody after okadaic acid treatment of lymphoid cells such as 697, 12B2 or RS11846 cells. Moreover, in the proB cells, RS(4:11) and MV(4:11) p53 protein were barely detected but phosphorylated forms of bcl-2 are easily detected.

It is well known that endogenous bcl-2 is not phosphorylated in follicular lymphoma cells (Alnemri, E.S., et al. (1992) *Proc. Natl. Acad. Sci. USA* 89:7295–7299, and Chen-Levy, Z., et al. (1989) *Mol. Cell Biol.* 9:701–710) in which the bcl-2 protein is activated by t(14:18) chromosomal translocation. Bcl-2 functions may be strictly regulated by an unidentified serine phosphatase(s) which presumably drives the equilibrium towards bcl-2 hypophosphorylation. This equilibrium is affected by treatment with okadaic acid, a phosphatase inhibitor or chemotherapeutic agents such as taxol. The presence of several potential phosphorylation sites in the bcl-2 molecule are known. Apparently, the maintenance of a delicate balance between phosphorylation and dephosphorylation is crucial for bcl-2 function. In order to prevent apoptosis, bcl-2 forms a heterodimer with an associated protein called Bax (Yin, X.M., et al. (1994) *Nature* 369:321–323; and Hengartner, M.O. and Horvitz, H.R. (1994) *Nature* 369:318–320) and is associated with another signal transducing protein called R-ras p23 (Fernandez-Sarabia, M.J. and Bischofft, J. (1993) *Nature* 366:224–225; and Haldar, S., et al. (1989) *Nature* 342:195–198). It is possible that hyperphosphorylation of bcl-2 may allow apoptosis through disruption of the bcl-2-Bax or bcl-2-R-ras p23 associations.

We claim:

1. A method of identifying compounds that modulate bcl-2 mediated cell death comprising the steps of:

contacting a cell with a test compound detecting whether bcl-2 in said cell is phosphorylated at a higher level or at a lower level compared to the level of phosphorylation of bcl-2 from a cell not contacted with said test compound; wherein phosphorylation of bcl-2 at a higher level in said cell contacted with said test compound indicates that the test compound modulates cell death by inducing cell death and phosphorylation of bcl-2 at a lower level in said cell contacted with said test compound indicates that the test compound modulates cell death by preventing apoptosis.

2. The method of claim 1 wherein said cell is lysed after contact with said test compound and phosphorylation of bcl-2 is detected by immunoblot using antibodies that bind to phosphorylated bcl-2.

3. The method of claim 1 wherein said cell is cultured in the presence of radiolabelled phosphorous and phosphorylation of bcl-2 is determined by detecting radiolabelled bcl-2.

4. The method of claim 3 wherein said radiolabelled bcl-2 is detected by immunoprecipitation using antibodies that bind to bcl-2.

5. The method of claim 4 wherein said radiolabelled bcl-2 is detected by immunoprecipitation using antibodies that bind to phosphorylated bcl-2.

6. A method of identifying compounds that modulate bcl-2 mediated cell death comprising the steps of:

preparing a cell extract from cells contacting said cell extract with a test compound detecting whether bcl-2 in said cell extract is phosphorylated at a higher level or at a lower level compared to the level of phosphorylation of bcl-2 from a cell extract not contacted with said test compound; wherein phosphorylation of bcl-2 at a higher level in said cell extract contacted with said test compound indicates that the test compound modulates cell death by inducing cell death and phosphorylation of bcl-2 at a lower level in said cell extract contacted with said test compound indicates that the test compound modulates cell death by preventing apoptosis.

7. The method of claim 6 wherein phosphorylation of bcl-2 is detected by immunoblot using antibodies that bind to phosphorylated bcl-2 in said cell extract.

8. The method of claim 6 wherein said cell extract is generated from cells cultured in the presence of radiolabelled phosphorous and the level of phosphorylated bcl-2 is determined by detecting radiolabelled bcl-2.

9. The method of claim 8 wherein said radiolabelled bcl-2 is detected by immunoprecipitation using antibodies that bind to bcl-2.

10. The method of claim 9 wherein said radiolabelled bcl-2 is detected by immunoprecipitation using antibodies that bind to phosphorylated bcl-2.

11. The method of claim 6 wherein said cell extract is contacted with said test compound in the presence of radiolabelled phosphorous and the level of phosphorylated bcl-2 is determined by detecting radiolabelled bcl-2.

12. The method of claim 11 wherein said radiolabelled bcl-2 is detected by immunoprecipitation using antibodies that bind to bcl-2.

13. The method of claim 11 wherein said radiolabelled bcl-2 is detected by immunoprecipitation using antibodies that bind to phosphorylated bcl-2.

* * * * *

UNITED STATES PATENT AND TRADEMARK OFFICE
CERTIFICATE OF CORRECTION

PATENT NO.   : 5,695,944
DATED        : December 9, 1997
INVENTOR(S)  : Carlo M. Croce and Subrata Haldar It is certified that error appears in the above-identified patent and that said Letters Patent is hereby corrected as shown below:

Column 1,
Between the title "MODULATION OF BCL-2 PHOSPHORYLATION" and the section heading "FIELD OF THE INVENTION", insert:
-- ACKNOWLEDGEMENT OF GOVERNMENT RIGHTS This invention was made with Government support under grant number R35 CA39860 awarded by the National Institutes of Health. The Government has certain rights in this invention. --

Signed and Sealed this

Ninth Day of October, 2001

Attest:

NICHOLAS P. GODICI
Attesting Officer   Acting Director of the United States Patent and Trademark Office